United States Patent [19]
Green et al.

[11] 3,937,066
[45] Feb. 10, 1976

[54] ULTRASONIC CAMERA SYSTEM AND METHOD

[75] Inventors: Philip S. Green, Redwood City; Hugh F. Frohbach, Sunnyvale; Louis F. Schaefer, Palo Alto; Joe R. Suarez, Fremont, all of Calif.

[73] Assignee: Stanford Research Institute, Menlo Park, Calif.

[22] Filed: Nov. 1, 1973

[21] Appl. No.: 411,729

[52] U.S. Cl. ............. 73/67.5 R; 73/67.7; 340/5 MP
[51] Int. Cl.[2] ......................................... G01N 29/04
[58] Field of Search ........... 73/67.5 R, 67.5 H, 67.6, 73/67.7, 67.8 R, 67.8 S, 67.9; 340/5 H, 5 MP

[56] References Cited
UNITED STATES PATENTS

| | | | |
|---|---|---|---|
| 3,226,721 | 12/1965 | Gould .................................... | 350/6 |
| 3,514,619 | 5/1970 | Ireland ................................... | 350/6 |
| 3,736,552 | 5/1973 | Sessler et al. ...................... | 340/5 MP |
| 3,778,756 | 12/1973 | Houston et al. ................... | 340/5 MP |
| 3,780,572 | 12/1973 | Rocha .............................. | 73/67.5 R |

OTHER PUBLICATIONS

P. S. Green et al., Acoustic Imaging in a Turbid Underwater Environment, Journal of Acoustical Society of America, Dec. 1968, Pp. 1719–1730.
E. E. Suckling et al., Image Scanner Using Diode Switching, Journal of Acoustical Society of America, Apr. 1969, pp. 892–894.
G. C. Knollman et al., Experimental Hydroacoustic Imaging System, Journal of Applied Physics, May 1971, pp. 2168–2180.
J. E. Jacobs, Ultrasound Image Converter Systems Utilizing Electron-Scanning Techniques, IEEE Transactions on Sonics and Ultrasonics, Vol. SU-15, No. 3, July 1968, pp. 146–152.

*Primary Examiner*—Richard C. Queisser
*Assistant Examiner*—John P. Beauchamp
*Attorney, Agent, or Firm*—Victor R. Beckman

[57] ABSTRACT

A lens converter ultrasonic camera method and system are shown for producing a visible representation in real time and true perspective of inhomogeneities in an opaque subject or specimen and especially suitable for imaging organs of living organisms. An ultrasonic wave generating transducer means is coupled to the specimen for insonification thereof, and focused perspective images using either transmitted or reflected ultrasonic waves are produced and directed upon an array of acoustic to electrical transducer elements. Scanning means are employed to expose the transducer elements to the entire acoustic image to generate electrical signals representative of the acoustic image. Amplified electrical signals representative of at least a portion of the acoustic image (such as a line thereof) are stored in individual electrical storage elements, which storage elements subsequently are connected, as by commutation means, to a utilization circuit, such as the control grid of a cathode ray tube, for intensity control of the indicating spot on the screen of the tube. The storage elements then are discharged, signals representative of another portion of the acoustic image are stored therein, and the cycle is repeated. The acoustic image scanning and recurrent wave generating and wave receiving operations may be performed at a periodically increasing and decreasing rate.

33 Claims, 8 Drawing Figures

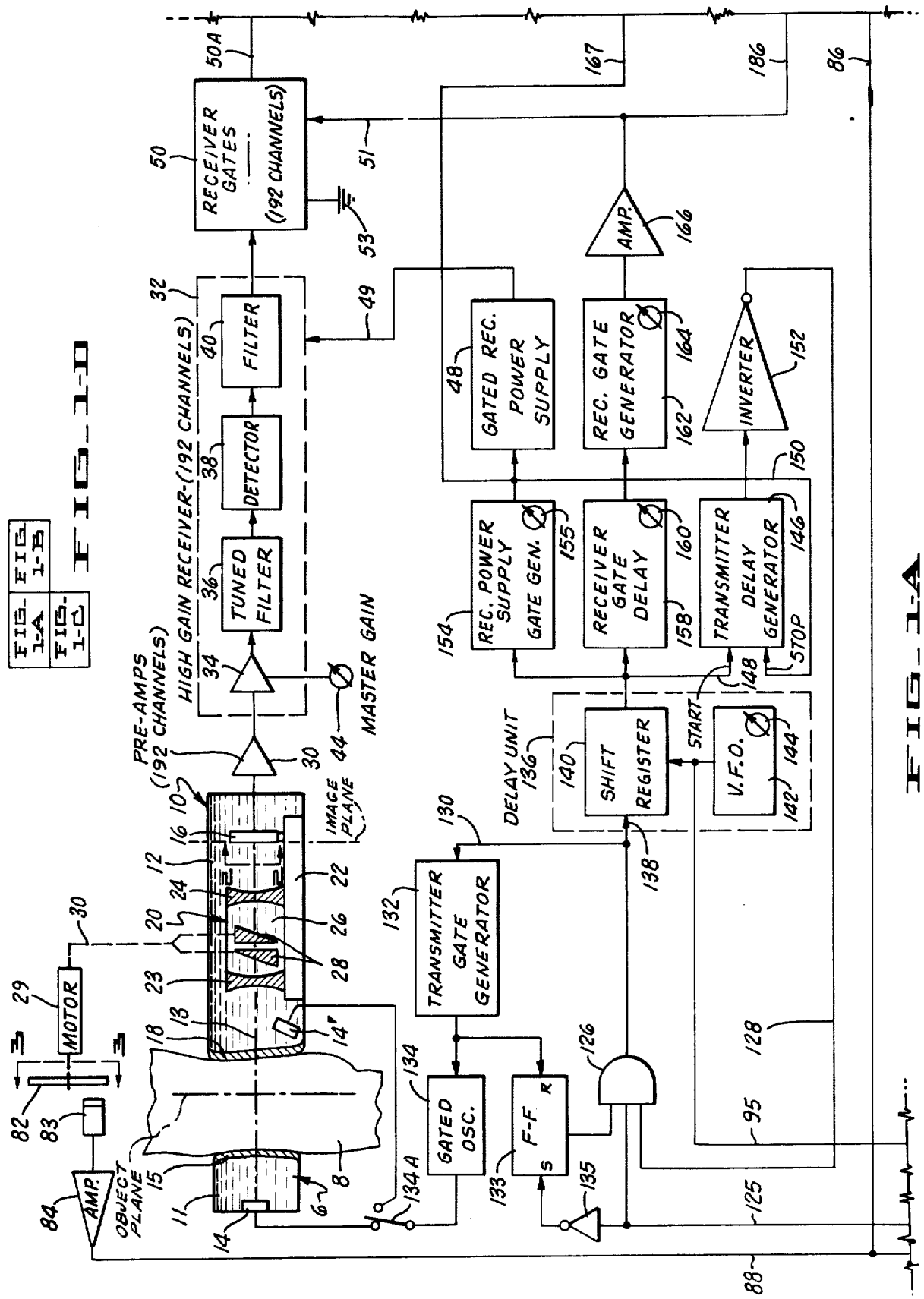

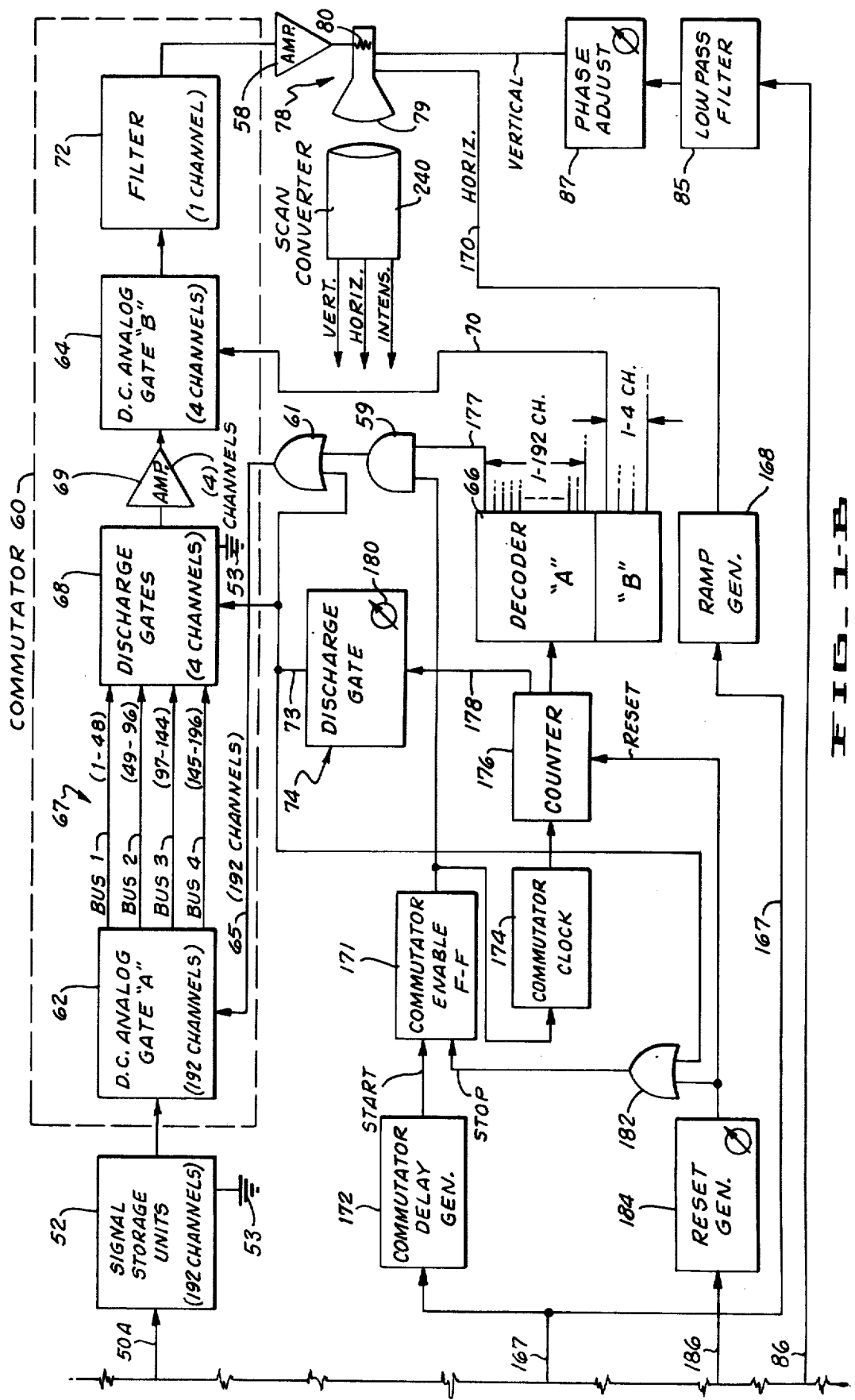
FIG. 1-B

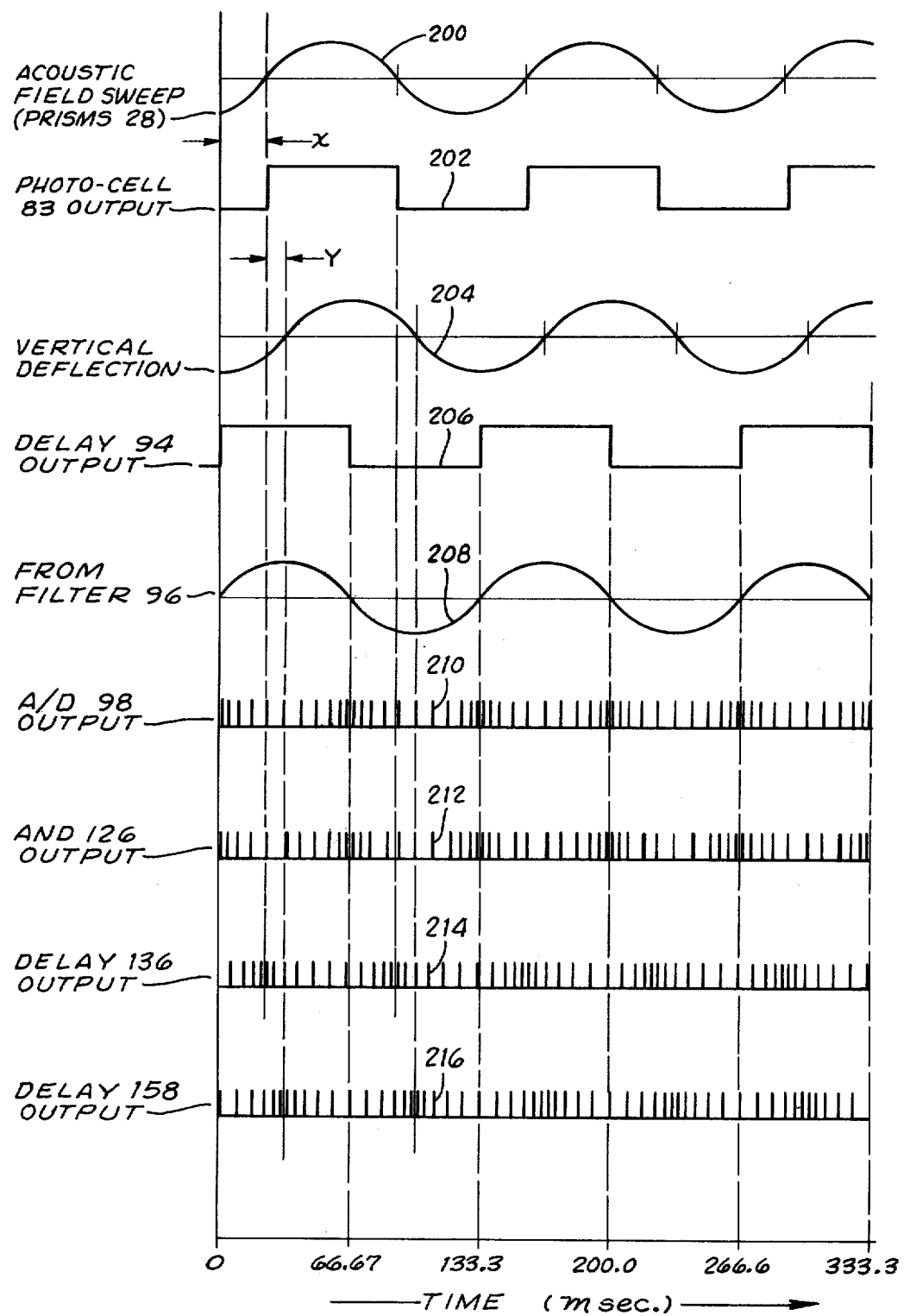
FIG_4

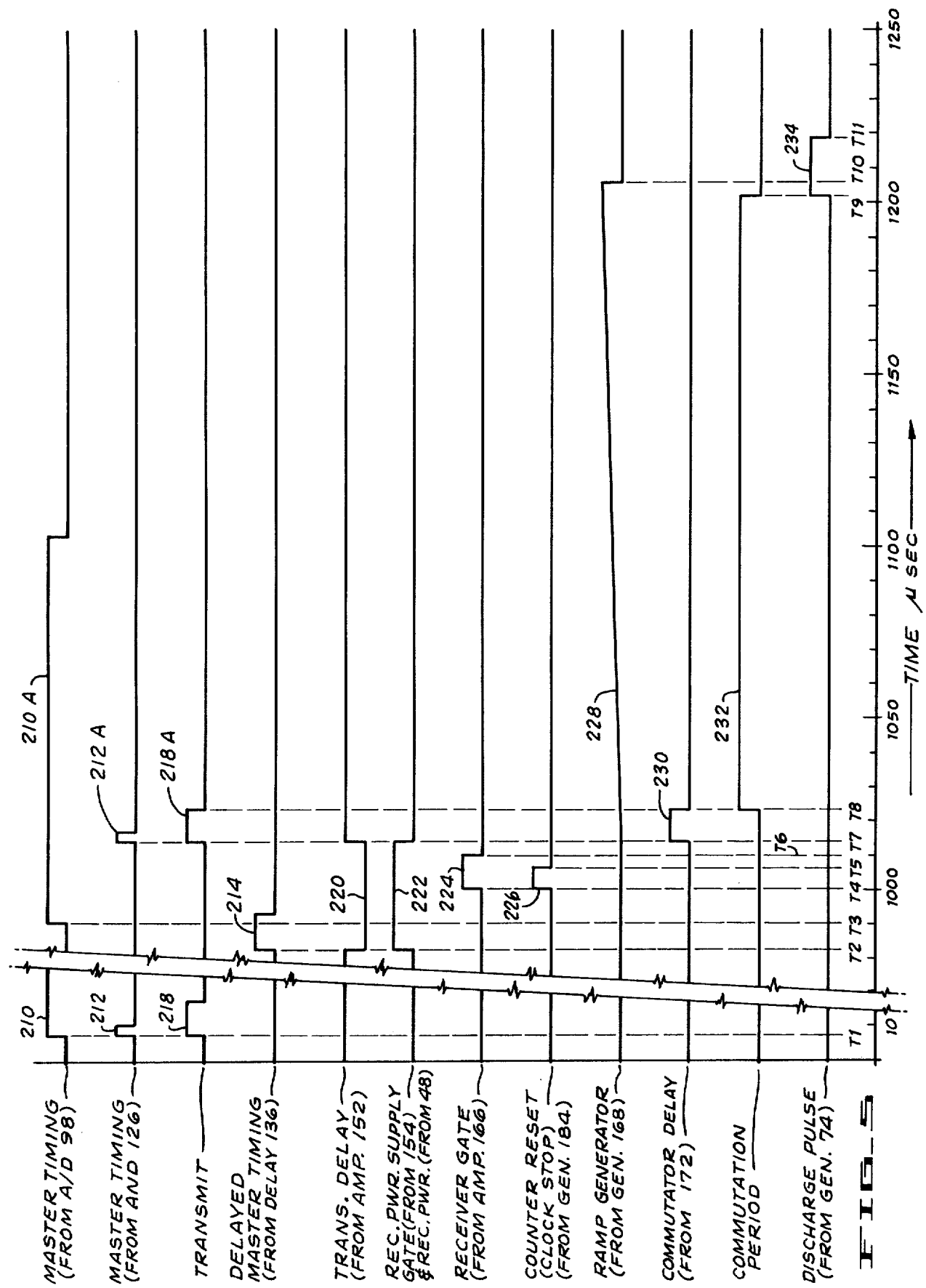

ULTRASONIC CAMERA SYSTEM AND METHOD

ORIGIN OF INVENTION

The invention described herein was made in the course of work under a grant or award from the Department of Health, Education and Welfare.

RELATED APPLICATIONS

This application is related to copending applications Ser. No. 270,274, filed July 10, 1972, Ser. No. 291,002, filed Sept. 21, 1972, Ser. No. 354,236, filed Apr. 25, 1973, now U.S. Pat. No. 3,913,061 Ser. No. 354,237, filed Apr. 25, 1973, now U.S. Pat. No. 3,849,698, and Ser. No. 363,876, filed May 25, 1973, now U.S. Pat. No. 3,886,490, all of which applications are assigned to the assignee of the present invention. The subject matter of these related applications is specifically incorporated herein by reference.

BACKGROUND OF THE INVENTION

This invention relates to viewing objects in optically opaque media and particularly to a method and apparatus for insonifying the subject and transforming reflected or transmitted ultrasonic waves directly into an optical image--an optical image capable of being viewed and reproduced by photographic means.

While ultrasonic viewing or exploratory systems have a wide range of applications and the methods and system described here may be employed in the full range of applications, the most exacting application, and the use for which the system is particularly suited, is that of imaging living organisms, e.g., organs such as the heart in a living human body. In view of the special applicability to medical uses, the description is cast in terms of this most exacting of applications but use of the methods and apparatus is not so limited.

The contemplated major application leads to a consideration of its competitors in terms of imaging internal organs in living organisms. Techniques which do not provide an image are not considered true competitors. Radiography does provide an image in some cases and has demonstrated that the presentation of diagnostic information in the form of an image bearing a one-to-one correspondence to the anatomy involved is a most powerful perceptual aid.

Although radiographic techniques are basically noninvasive, in many cases catheterization or injection of contrast media is required for effective visualization. Always present are the risks of exposure to ionizing radiation, both to the patient and to the radiologist. Additionally, there are many situations in which x-rays fail to provide adequate visualization of tissues and organs. In such cases, the diagnostician must depend more heavily on other established means— physical examination, chemical tests, measurement of electrical potentials, etc. For example, the normal thyroid gland is not demonstrable on x-ray studies; the abnormal gland is demonstrated only when it contains calcified areas or by its effect on neighboring structures. Present methods of diagnosis cannot adequately distinguish malignant from nonmalignant thyroid growths.

Radiographic techniques have proven deficient in visualization of the brain, some bone structure and detecting tumors in regions such as the breast. Specifically, radiographic visualization of the brain is carried out by visualizing its ventricles and basal cisterns with the injection of opaque media or gas, with the risks that attend the procedure. Arterial dye injections are required to visualize the heart and circulatory system, which is otherwise demonstrable only when calcification is present. Many details of the internal structures of abdominal organs are not apparent in simple radiographic examination; the pancreas, for example, cannot be distinguished from the surrounding soft tissues. Again, contrast media, either for absorption by the organ's tissue or passage through its circulatory system, are required in order to delineate the organ.

Radiographic visualization of the bones in the extremities is satisfactory for most purposes. However, visualization of the soft tissue, cartilage and joint cavities of the extremities cannot be adequately performed with any x-ray technique.

Mammography—a radiographic technique for detecting tumors of the breast—has found increased acceptance. However, in order to detect the minute calcifications that occur in malignant tumors, very high resolution film is used without intensifying screens. This film is relatively insensitive and requires long exposure. Thus a considerable dose of the readily absorbed soft x-rays is delivered to the patient. The inadequate interaction of x-rays with soft tissue and the complications associated with the use of contrast media significantly restrict the application of radiography. A further disadvantage of x-rays is that they interact only with tissue volume and are insensitive to interfaces between tissues. There is a clear need for new procedures by which internal organs can be visualized without using ionizing radiation and without introducing foreign material into the body.

The ability of ultrasonics to differentiate tissues on the basis of their elastic properties, the lack of toxic effects at energy levels required for diagnostic use and the fact that there is no requirement for invasive techniques with their attendant disadvantages and dangers make ultrasonic visualization a particularly attractive and effective diagnostic tool. A variety of ultrasonic techniques have been demonstrated. A discussion of the various methods and their capabilities is found in INTERNATIONAL JOURNAL OF NONDESTRUCTIVE TESTING, vol. 1 (1969), pp. 1–27, "Methods of Acoustic Visualization," by Philip S. Green, one of the present inventors. Although the referenced article gives a rather complete discussion, and its subject matter is specifically incorporated herein by reference, a discussion of the techniques is given here to establish the background of the present invention.

The ultrasonic technique first introduced and now most widely used in diagnostic medicine is the sonar-like method wherein an ultrasonic transducer in contact with the patient's skin launches ultrasonic pulses into the tissue and subsequently detects their reflections from tissue interfaces. The method is labeled the "A-scan" technique. Since the round trip travel time of a reflected pulse is proportional to the distance from the transmitter to the reflecting layer, the presentation of these wave trains on an oscilloscope permits the operator to directly measure these distances. This method has found wide acceptance as an indicator of midline displacement caused by tumors of the brain.

Aside from doppler methods, in which tissue or fluid motion is detected by means of the frequency shift it imparts to reflected ultrasonic waves, the only other method of diagnostic ultrasound to achieve a significant level of use is the so called "B-scan." As with the A-scan, the B-scan method of ultrasonic diagnosis employs a narrow beam transducer to project a short ultrasonic pulse into the tissue and to detect the reflected pulses. In B-scan, however, a two dimensional image is produced by moving the transducer slowly past the area of interest and recording the reflected pulse trains at closely spaced intervals. A cathode ray tube display is used in which one of the orthogonal deflection voltages is proportional to the transducer position and the other to the time elapsed since the last pulse was transmitted. The reflected ultrasonic pulses intensity-modulate the display. The resulting image is of a section of the body or organ that lies in the plane of the propagating rays.

The success of B-scan imaging has been most striking in obstetrics. Cross sections of the fetal head, thorax and limbs can be displayed with enough clarity to determine fetal size and position. B-scan is also useful in the differentiation of abnormal and normal pregnancy and for localization of the placenta.

Application of B-scan to the abdominal organs has met with more modest success. It is frequently possible to detect the presence of an abnormal state in the liver. However, except for the differentiation of cystic and solid masses, it is rarely possible to identify the abnormality. It is generally recognized that practical application of ultrasound for diagnosis of liver diseases is hampered by both inadequaces in equipment and examining techniques. The B-scan technique has been used successfully to measure the volumes of both liver and spleen.

B-scan has been employed for the measurement of cross sectional area in many organs, including the kidney and bladder. Again, although echoes are frequently observed from the interior of diseased kidneys, it is seldom possible to correlate these echo patterns with any specific pathological change.

In a B-scan study of the thyroid, four basic types of echo patterns have been distinguished and, in some cases, correlated with specific pathologies. It is found that cystic nodules rarely produce ultrasonic echoes. The results with solid adenomas are much less consistent; in the case of colloid adenoma, the ultrasonic "tomograms" are often echo free in the thyroid area. Almost all of the carcinomas investigated have been papillary, and their tomograms typically contained many echoes, although they were divided between two of the designated patterns. Nonneoplastic lesions—for the most part diffuse thyroiditis and Graves' disease—are not well characterized by the tomograms.

Detection of neoplasms with the B-scan technique has been reported. As with most other organs, differentiation can be made between cystic and solid masses. Although this early work gave rise to hope that distinctive echo patterns were associated with malignant and benign solid masses, it is the opinion of many investigators that this differentiation cannot be made on the basis of B-scan images. Visualization of the breast in this manner is further complicated by the extent and variability of sonic scattering by the internal structure of the normal breast.

Application of B-scan to visualization of the brain is hampered by the considerable reflection and refraction of sound that occurs at the skull. Relatively little work had been done in this area until recently, when in several investigations it was shown that some structures within the brain can be delineated if care is taken to discriminate against secondary reflections from the skull.

Image-like visualization of the heart is achieved by holding the transducer still while recording the output on a moving strip chart recorder. In this manner, motion of the heart wall and mitral valve results in wavy lines in the recording. The amplitude of these oscillations is a direct measure of valve and wall displacement, while valve and wall thickness can be deduced from the thickness of the lines. The heart structures are not actually resolved with this technique.

Although many other organs have been visulaized visualized B-scan, the only one of these to have received intensive investigation is the eye. Tumors of the eye and retinal detachments are readily displayed, as is some of the normal structure of the eye.

B-scan has established the potential effectiveness of ultrasonic visualization in medical diagnosis and is particularly effective for determining cross sectional shapes and areas of internal organs. However, B-scan has several significant inherent deficiencies of which the following are noteworthy:

Poor lateral resolution: In order to ensure that the ultrasonic beam is well collimated, it is necessary to use a transducer that is many wavelengths in diameter. The lateral resolution is limited to the transducer diameter—typically 0.5 to 2 cm. If a highly focused transducer is used, a sharp focus will prevail at the focal depth, while at other depths the image will be grossly out of focus.

Difficulty with specular reflection: Often tissue interfaces have relatively little irregularity on the scale of the ultrasonic wavelength (usually 0.3 to 1.0 mm) and thus reflect waves in a specular or mirror-like manner. It has become general practice to sector scan the transducer rapidly as it transverses the area of interest so that reflections from specular surfaces are less likely to be undetected. However, this provision effects only a partial solution to the specularity problem while introducing a great deal more complexity.

Insensitivity to local variations in acoustic absorption: The differences in acoustic absorption between normal and abnormal tissues may in some cases be a more sensitive indicator than differences in acoustic impedance. The pulse echo methods are essentially insensitive to local variations in absorptivity.

Long "build-up" time of image: Because of the finite time required for a transmitted pulse to return from the most distant portion of the organ and because of mechanical complexity, the time required to build up a single cross sectional image may be several minutes. Not only must the patient be kept immobile during this time to prevent image smear, but the diagnostician must forego the considerable advantage of seeing an image in "real time." Furthermore, five to ten scans are usually required to completely characterize an organ.

Low dynamic range: Although tissue reverberations span a wide range of amplitudes, the storage tube display typically used in B-scan imaging presents only a two level (black-white) approximation of the image.

In an effort to overcome the problems of the A-scan and B-scan techniques for diagnostic visualization, two other techniques of ultrasonic visualization have been investigated, viz., the lens/converter method and acoustic holography. An important distinction between the results obtained with the B-scan method and those obtained with both lens/converter and acoustic holography methods is found in the type of image produced.

Whereas the B-scan image is of a section of the object lying in the plane of the propagating rays, the image produced with lens/converter and acoustic holography systems is of a plane (or planes) normal to the propagation direction. The latter's similarity to our everyday experience of visualization leads to greater ease of interpretation. Furthermore, while B-scan images are formed with reflected energy only, images may be produced with either transmitted or reflected energy by using the lens/converter method or acoustic holography method, in analogy to the two most common modes of optical microscopy. A theoretical foundation for the lens/converter mode of acoustic image formation is found in P. S. Green, J. L. S. Bellin and G. C. Knollman, "Acoustic Imaging in a Turbid Underwater Environment", J. ACOUST. SOC. AM., vol. 44 (1968), pp. 1719–1730.

Considering the lens/converter method, the use of lenses or focusing reflectors to concentrate ultrasonic energy is well known. A close analogy exists between the reflection and refraction of acoustic and optical wavefronts at boundaries separating regions of different refractive index, and sonic lenses and reflectors are designed in accordance with the same procedures used in optics. Indeed, the analogy between acoustics and optics extends to all scalar propagation phenomena. Then, as we might expect, there exists for an acoustic lens or focusing reflector an image plane/object plane relationship identical to that found in optics. Specifically, a spatial pattern of acoustic pressure in a plane in front of an acoustic lens (and propagating toward it) will induce in the conjugate plane of the lens a diffraction and aberration limited replica of itself. As in optics, this replica may be a virtual image for certain parameter values. A real image of an insonified object is formed if the object is placed beyond the focal plane of a convergent lens. An acoustic image converter placed in the corresponding image plane (as determined by the lens law) will detect a focused acoustic image of the object. The method and apparatus for ultrasonic imaging which constitute the present invention are a lens/converter system.

As pointed out above, the acoustic holography method of imaging can produce images of the same form as those resulting with the lens/converter system. In the case of holography, the acoustic lens may be omitted, and the wavefield scattered by the object is sampled directly by the converter. An optical transparency representing this wavefield is then formed by one of several conversion methods. Illumination of this transparency by a laser produces both a real and virtual image of the insonified object.

In recent years the holographic method of acoustic visualization has received considerable attention. Various methods of implementation have been demonstrated. The holographic approach, however, has been found to have several serious drawbacks. The formation of a holographic reconstruction requires first that the ultrasonic wavefield be recorded on film and that the film be developed; this is a time consuming operation producing a single image and is incompatible with the desired real time viewing capability. Although real time holography is possible with a liquid surface relief conversion method, this method is considered too insensitive for diagnostic use, a judgment based on laboratory experience with the liquid surface relief conversion process as used to make nonholographic, real time, in vitro images of various organs. Although work is now in progress to develop real time, electronically addressable transparencies for acoustic holography, results to date have been discouraging. A further disadvantage of ultrasonic holography is that coherent ultrasonic waves must be used for object insonification. It has been our experience, substantiated by theoretical studies, that broadband sound produces images of greater fidelity. Although in optical holography the reconstructed image is seen in three dimensions, this advantage is not realized in the acoustic case, owing to the inherent distortion caused by the large disparity between the wavelengths of ultrasound and light.

SUMMARY OF THE INVENTION AND OBJECTS

The present invention relates to a method and apparatus for producing a visible representation in real time and true perspective of inhomogeneities in an opaque subject or specimen which are particularly suited for imaging organs in living organisms. The camera system includes a lens/converter system and means for insonifying the subject. The lens/converter system includes a lens which receives sound waves either transmitted to or reflected from the subject and focuses them on a converter located in the image plane. The converter, in turn, transforms the sound waves to electrical signals that are electronically processed and converted to a real time optical image of the area of interest.

It is an object of the invention to produce two dimensional perspective images of soft tissue structures that cannot adequately be visualized by any radiographic technique.

Another object of the invention is to produce such images in real time with high resolution.

BRIEF DESCRIPTION OF DRAWINGS

FIGS. 1A, 1B and 1C taken together, as shown in FIG. 1D, show a combination block and schematic diagram embodying the ultrasonic camera system and method of this invention;

FIG. 2 is a sectional view taken along line 2—2 of FIG. 1A and showing the linear array of receiver transducer elements;

FIG. 3 is a sectional view taken along line 3—3 of FIG. 1A and showing means for generating recurrent timing signals; and FIGS. 4 and 5 are waveform diagrams of electrical signals developed at various locations within the system and showing relative timing thereof, the time scale employed in the FIG. 5 waveforms being much shorter than that in FIG. 4.

DESCRIPTION OF PREFERRED EMBODIMENT

Figures 1C, 2, 3:
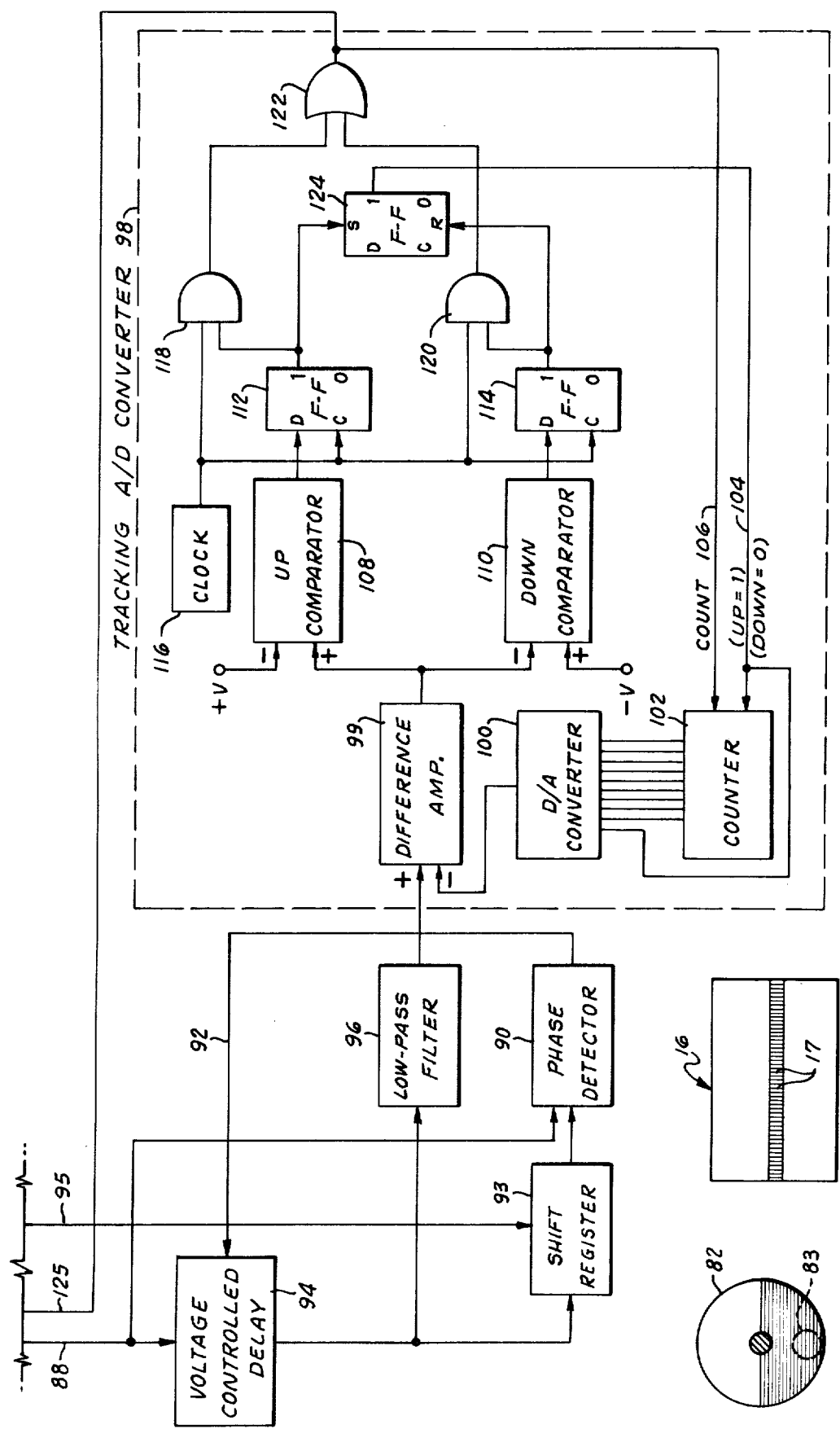

Reference first is made to FIG. 1A wherein there are shown an acoustic transmitting unit 6 used to insonify a subject 8 and an acoustic camera or receiving unit 10 which receives and focuses the compressional wavefield from the insonified subject and translates said wavefield into electrical signals which are converted into a real time visual display of the insonified subject at the face of a cathode ray tube 78 (FIG. 1B).

Both the transmitting and receiving units 6 and 10 are filled with a suitable acoustic transmission medium 11 and 12 (e.g., water) for the support of acoustic waves produced by an ultrasonic wave generating transducer 14 located at one end of the transmitting unit 6. A liquid tight acoustically transparent window 15 closes the other end of the transmitting unit. Ultrasonic compressional waves generated by the transducer 14 are transmitted through the medium 11 and coupled through the sonically transparent window 15 to insonify the subject 8.

The ultrasonic compressional wavefield from the subject 8 is coupled through a liquid tight acoustically transparent window 18 at one end of the receiving unit 10 to the liquid medium 12 within the camera body. A composite acoustic lens assembly 20 is located in the liquid medium 12 between the window 18 and an acoustic receiving transducer 16. The transducer 16, as seen in FIG. 2, may comprise a linear array of piezoelectric elements 17 individually responsive to the instantaneous field pressure thereat. In an exemplary arrangement which has been built and tested, 192 such piezoelectric elements have been included in the array, but it will be apparent that the invention is not limited to such an array. Although not seen in the drawings, the array may be arranged in an arc, as viewed from above, to better fit a single line across the compressional acoustic image field. It will here be noted that operation in the reflective mode also is possible by use of an ultrasonic wave generating transducer means 14' located, for example, in the fluid 12 of the receiving unit for insonifying the subject 8. Reflected rather than transmitted ultrasonic waves from the insonified object are processed when the transducer means 14' is employed.

The composite acoustic lens assembly 20 serves the dual function of focusing the acoustic waves from the insonified subject and of periodically deflecting the waves up and down to move the compressional acoustic image field past the receiving array 16. To these ends, the lens assembly includes a pair of axially spaced lens elements 23 and 24 with a fluid filler medium 26 contained therebetween. A pair of rotatable acoustic prisms, or wedges, 28 is located in the filler medium in axial alignment with the lens elements. The prisms are rotated in opposite rotational directions at the same angular speed by means of a motor 29 coupled thereto through suitable mechanical linkage 30. When the prisms are rotated in the above described manner by the motor, the compressional image field is sinusoidally swept past the line of acoustic receiver elements 17 in the array 16. With the illustrated arrangement the field is swept once in each vertical direction for each full rotation of the acoustic prisms 28 without lateral displacement of the field. A composite acoustic lens for focusing purposes shown in patent application Ser. No. 270,274, filed July 10, 1972, an acoustic imaging and image deflecting system shown in patent application Ser. No. 354,236, filed Apr. 25, 1973, and a linear array transducer shown in patent application Ser. No. 291,002, filed Sept. 21, 1972, may be employed in the acoustic camera system and method of this invention. The teachings found in these applications are employed herein for the same purposes and the subject matter of these applications is specifically incorporated herein by reference.

The transducer 16 and lens assembly 20 are attached a fixed distance apart to a base 22, which base is longitudinally movable within the camera body. Focusing at any desired level within the specimen or body 8 is accomplished by movement of the lens assembly and transducer along the acoustic axis 13 to place the body part to be observed at the object plane of the lens assembly. In the exemplary embodiment the transmitting unit 6 also is movable along the axis 13 to accommodate body parts of different thickness. In an alternative arrangement, not shown, the receiving transducer means 16 may be mounted independently of the lens assembly 20, such that the lens assembly without the transducer means 16 is longitudinally movable within the camera body for focusing at any level within the body 8. With such an arrangement the size of the acoustic image field swept past the transducer elements 17 will vary depending upon the distance between the transducer elements 17 and lens assembly 20.

The electrical signals generated by the piezoelectric elements 17 of the linear array 16 are supplied to preamplifiers 30 which preferably are physically located adjacent the array to minimize the length of necessary connecting leads. With an array of 192 piezoelectric elements, there are required 192 preamplifiers 30, one for each transducer element signal. The block 30 thereby represents 192 preamplifiers and the solid line connections to and from the block illustrate the connections for all 192 preamplifiers.

The 192 preamplifier outputs are supplied individually to 192 high gain receivers 32 of identical design. Each receiver comprises a variable gain amplifier stage 34 having an output which is fed to filter 36 tuned to the frequency of the ultrasonic wave generated by the transmitting transducer 14. Single frequency signals as well as broadband signals may be employed. Alternatively, different frequency pulses may be used. Regardless of the frequency or frequencies employed, ultrasonic waves within the range of, say, 1 to 10 MHz are typical. The amplified and filtered signal is detected by a detector 38, such as a full wave detector, and the high frequency component of the detected signal then is removed from the demodulated signal by a low pass filter 40. The high gain receivers 32 may operate in either a linear or a nonlinear mode. For example, the illustrated receiver which operates in a linear mode may be operated substantially logarithmically by simply including a feedback loop between the filter 40 output and the variable gain amplifier 34 input. Switching between such modes of operation may be under control of a switching element in the feedback loop. Operation in the logarithmic mode results in a greater dynamic range of input signals to be displayed for improved visual representation of the wavefield. A log/linear control, not shown, for control of the amplifier mode of operation and a master gain control 44 for setting the gain of all of the amplifiers 34 may be included at the operating console, or panel, of the camera system. In the pulse mode operation of the camera system exemplified in the drawings, the receivers 32 are supplied with power during only a portion of each operating cycle from a gated receiver power supply 48 connected to the receivers over line 49. Timing of the gated receiver power supply operation is described hereinbelow in the description of the novel method of this invention.

The outputs from the high gain receivers 32 are fed through receiver gates 50 and thence over lines 50A to signal storage units 52 (FIG. 1B). In the 192 channel system such as illustrated, 192 receiver gates and storage units are represented by each of the blocks 50 and 52. Each of the receiver gates 50 may comprise a DC analog gating circuit, the opening and closing of which is under control of a receiver gating signal supplied thereto over line 51. The receiver gates serve to switch the receiver output to the storage units when the gates are opened during receipt of a gate control pulse on line 51 and to bypass the receiver outputs to the common ground 53 when the gate is closed. The signal storage units 52 each may comprise a capacitor connected between the receiver gate and common ground, which capacitor is charged to a level determined by the receiver output when the receiver gates are opened. The capacitors maintain the charge without appreciable leakage until after sampling of the stored signals by a commutator 60 is completed.

After the signal storage units 52 have been simultaneously charged by gated signals from the receivers 32, the receivers are turned off by removal of power thereto from the power supply 48 and the storage units are sequentially sampled by the commutator 60 for application of a composite video signal to the input of video amplifier 58. A commutator 60 of novel design is employed to reduce the adverse capacitance effects which normally would be present in the connection of 192 information channels to a single line at the input to the video amplifier. The illustrated commutator includes cascade connection DC analog gate circuits (A) and (B) identified by the blocks 62 and 64. The block 62 represents 192 analog gate circuits, the opening and closing of which are sequentially controlled by commutator gate control signals supplied thereto over lines 65 from the "A" section of a decoder 66 through AND and OR gates 59 and 61, respectively. Each block 59 and 61 represents 192 AND and OR gates, respectively, and the lead 65 represents 192 lines from the individual OR gates to the 192 individual gate circuits 62. The gate circuits 62 have four output buses 67, shown as Bus-1 through Bus-4, which handle signal channels 1–48, 49–96, 97–144 and 145–192, respectively.

The four signal channels from the gate circuits 62 are fed through analog discharge gates 68 and amplifiers 69 to the input of the second commutator gate circuits 64. The blocks 68, 69 and 64 represent four discharge gate circuits, amplifiers and analog gate circuits, respectively. The discharge gates 68 normally are open for passage of the signals from the first analog gate circuits 62 to the amplifiers 69 and thence to the second analog gate circuits 64. Opening and closing of the analog gate circuits 64 are sequentially controlled by commutator gate control signals supplied thereto over lead wires 70 from the "B" section of the decoder 66. The four gate circuits 64 are switched at the same rate that the buses 67 are sequentially supplied with signals from the first analog gate circuits 62. The four signal channels are combined at the output from the analog gate circuits 64 and supplied to a filter 72 to filter therefrom noise produced by the commutation process. The resultant composite signal output from the filter 72 is supplied to the input of the video amplifier 58 and thence to the cathode ray tube 78.

When the information contained on all 192 signal storage elements 52 has been sequentially applied to the video amplifier 58 through the commutator, the storage elements 52 are discharged to ground in preparation for the next signal storage operation. Discharge of the storage elements may be effected substantially simultaneously by the opening of all 192 analog gate circuits 62 and closure of the four discharge gate circuits 68. A discharge gate control signal at the line 73 from a discharge gate generator 74 is applied both to the analog gate circuits 62 (through the 192 OR gates 61) to open the same and to the four discharge gates to close the same. The charges contained in the signal storage units 52 are thereby passed through the commutator gate circuits 62 and thence bypassed to ground 53 through the discharge gate circuits 68.

The output from the video amplifier 58 is supplied to a utilization circuit such as a cathode ray tube 78. In the illustrated arrangement the amplifier output is supplied to the control grid 80 of the tube for density control of the electron beam directed onto the face, or screen, thereof. An inverter circuit, not shown, may be switched into and out of operation in the connection of the video signal to the cathode ray tube for selection of either a "positive" or "negative" type of image of the acoustic field at the face of the tube.

A master timing signal for synchronization of the various camera system functions is obtained by means of a timing disk 82 attached to the motor 29 shaft for synchronous drive operation of the disk with the counterrotating prisms, or wedges, 28. In the illustrated arrangement, as seen in FIG. 3, one half of the disk is of one color and the other half is of another color. A photocell 83 located adjacent the disk produces an output signal in response to one of the colors for generation of a series of pulses of equal on and off time periods. As noted above, for each revolution of the counterrotating prisms 28 the acoustic image field is swept past the line of transducer elements 17 once in each direction, during which time a squarewave signal is produced at the output from the photocell 83. For purposes of description only, the disk 82 and counterrotating prisms 28 may be driven at, say, 450 revolutions per minute by the motor 29, whereby the acoustic image field is swept at a rate of 7.5 complete (i.e., up and down) sweeps per second and timing signals are produced at a rate of 7.5 pulses per second.

In the waveforms of FIG. 4 the sinusoidal sweep of the acoustic image field by the counterrotating prisms is identified by the waveform 200, the ends of the sweep occurring at the peaks and valleys of the sinewave 200. The photocell 83 output, identified by the waveform 202, comprises a symmetrical squarewave signal having leading and trailing edges at the center of the acoustic image sweep where the deflection thereof is zero. Generation of the squarewave signal 202 at the appropriate time is achieved by the proper physical positioning of the photocell with respect to the rotating disk 82 and connection of the disk to the motor 29 shaft.

The squarewave photocell output is amplified by amplifier 84 (FIG. 1A) and used, inter alia, in the production of a deflection voltage for the cathode ray tube 78. To this end the squarewave signal is converted to a sinewave by passing the same through a low pass filter 85 (FIG. 1B) over line 86. The sinusoidal signal from the low pass filter is fed through an adjustable phase control circuit 87 and supplied to one of the deflection circuits of the cathode ray tube 78 for scanning in one orthogonal direction across the face, or screen, thereof. In the illustrated arrangement this sinusoidally varying voltage is supplied to the vertical deflection plates of the tube. The phase control circuit 87 is adjusted for proper synchronization of the vertical sweep with the composite video signal applied to the intensity control electrode of the tube during the commutation process. The sinewave vertical deflection voltage is identified by reference numeral 204 in the FIG. 4 waveform diagram.

The transmitting and receiving system described above thus far may be operated periodically at a constant repetition rate wherein the horizontal deflection ramp voltages are periodically applied to the horizontal deflection plates of the cathode ray tube 78. The combined use of a sinusoidal vertical deflection voltage with a periodic ramp horizontal deflection voltage would result in a raster of unevenly spaced horizontal sweeps across the face of the tube, with a resultant uneven intensity on the face of the screen. Compensation for such changes in intensity could be made by periodically varying the intensity of the electron beam to reduce the intensity at the extreme excursions of the vertical deflection 204.

In the exemplary arrangement the transmitting and receiving units are oppeated at a sinusoidally varying rate in synchronism with the sinusoidal sweep of the acoustic image field by the counterrotating prisms for production of evenly spaced horizontal sweep lines at the face of the cathode ray tube. In addition to being used to produce the sinewave vertical deflection signal in the manner described above, the amplified squarewave master timing signal from the photocell 83 also is employed in the production of master timing pulses for control of transmitter andd receiver operations at a rate which varies sinusoidally at the same sinusoidal rate at which the acoustic image field is swept by means of the counterrotating prisms 28. To this end, the amplified squarewave signal from the amplifier 84 (FIG. 1A) is applied over line 88 to a voltage controlled delay unit 94 (FIG. 1C) comprising, for example, a one-shot having a pulse duration dependent upon the magnitude of a control voltage supplied thereto from a pulse detector 90 over line 92. The phase detector and voltage controlled delay unit are included in a phase lock loop which includes also a shift register 93 supplied with clock pulses from a variable frequency oscillator 142 (FIG. 1A) over line 95.

The shift register 93, which is triggered by the trailing edge of the output pulses from the voltage controlled delay unit 94, functions as a variable delay unit and provides output pulses which are delayed in an amount inversely related to the clocking frequency. The shift register output and amplified squarewave at the input to the voltage controlled delay unit 94 are supplied to the phase detector 90. Consequently, the pulse delay provided by voltage controlled delay unit 94 is equal, but opposite, to that provided by the shift register 93 in the balanced loop condition. In practice, as will become apparent below, the squarewave signal from the photocell 83 is delayed by delay unit 94 an amount such that the leading and trailing edges of the squarewave signal lead the acoustic field sweep at the instant that the sweep reaches its upper and lowermost ends by an amount substantially equal to the transmit time of the ultrasonic pulses in traveling between the transmitting transducer 14 (or 14') and the counterrotating prisms 28 via the subject 8. As noted above with reference to FIG. 1A, this distance is variable to permit focusing at different levels within the body 8 and to accommodate different thickness specimens. The delay provided by the delay unit 94 is varied accordingly by control of the frequency at which the shift register 93 is clocked. In the waveform diagram of FIG. 4 the squarewave output from the voltage controlled delay unit 94 is identified by reference numeral 206, which waveform leads the photocell output 202 and acoustic field sweep by a time designated $x$, equal to the transit time of the acoustic wave from the transmitter transducer 14 (or 14') to the acoustic field deflecting prisms 28. In the waveforms of FIG. 4 is greatly exaggerated time $x$ is shown for purposes of clarity of illustration. In practice, a transit time $x$ on the order of, say, 0.50 to 1.5 milliseconds is typical.

The squarewave signal from the delay unit 94 is converted to a sinewave by passing the same through a low pass filter 96. This sinewave output, identified by reference numeral 208 in FIG. 4, is supplied as an input to a tracking analog to digital (tracking A/D) converter 98. Tracking A/D converters include an up-down counter having an output which is made to track the analog input, which counter output is taken as the output of the converter. In the present arrangement, as will become apparent from the following description, the pulses which drive the up-down counter are employed as master timing pulses. Therefore, with a sinewave input the converter output is employed in the present invention comprises pulses which occur at a rate which varies sinusoidally at the rate of the sinusoidal input signal. The number of pulses produced per sinewave cycle depends upon the amplitude of the sinewave signal input. In the illustrated arrangement, for purposes of description only, the sinewave amplitude and operating characteristics of the tracking A/D converter are such that 400 pulses are produced at the output from the converter during one complete cycle of the sinewave input.

Tracking A/D converters are well known and require no detailed description. A satisfactory converter 98 may comprise a differential operational amplifier 99 having as one input the sinewave signal from the low pass filter 96 and as a second input the output from a digital to analog (D/A) converter 100 which is actuated by an up-down binary counter 102. In operation the counter alternately counts up and down under control of an up-down signal supplied thereto over line 104 and counting pulses supplied thereto over line 106. The analog input signal is compared in the differential amplifier to the output from the D/A converter 100, and the differential amplifier output is supplied to a pair of differential comparators 108 and 110, which are supplied also with equal magnitude and opposite polarity threshold potentials $+V$ and $-V$, respectively. No output from the comparators is produced until the input signal thereto (of one polarity) exceeds the opposite polarity threshold potential. If, for example, the sinewave signal input to the converter is increasing, the up comparator 108 is triggered when the output from the differential amplifier exceeds the magnitude of the threshold voltage. The comparator outputs are supplied to type D flip-flops 112 and 114 which have an output at the 1 terminal whenever signals are simultaneously present at the input terminals. A clock 116 provides clock pulses to the C terminals of the flip-flops.

The 1 outputs from the flip-flops 112 and 114 are connected through AND gates 118 and 120 to an OR gate 122. Output pulses from the tracking A/D converter 98 are obtained from the OR gate 122. The OR gate 122 output also is fed back to the counter 102 over line 106 to drive the same. Up-down control of the counter is provided by the output from flip-flop 124 over the line 104. The flip-flop 124 is set and reset by signals from the 1 terminals of the flip-flops 112 and 114, respectively.

For purposes of description of the operation of the tracking A/D converter, assume that the sinewave signal input thereto is increasing. The up comparator 108 thereby produces an output when the output from the differential amplifier exceeds the threshold voltage. The flip-flop 112 is thereby triggered upon the occurrence of the subsequent clock pulse to produce an output at the 1 terminal which is supplied to the AND gate 118. The simultaneous application of a clock pulse and the output from the flip-flop 112 to the input of the AND gate cause the output therefrom to go to a high condition. Normally, both inputs to the OR gate 122 are low such that the output therefrom is low. Therefore, when the one input goes high, the output goes high to provide a pulse output therefrom. This output pulse also causes the counter 102 to step, thereby increasing the output from the D/A converter 100. The input to the differential comparator 108 from difference amplifier 99 thereby is reduced to an equilibrium level.

Up counting by the counter 102 continues until the sinewave input from the low pass filter 96 reverses direction. When the differential amplifier 99 output exceeds the threshold voltage −V, the down comparator 110 is triggered to operate the flip-flop 114 which, in turn, resets the flip-flop 124 and actuates the AND gtes 120 and the OR gate 122. The tracking A/D converter circuit thereby counts down and continues to do so until the sinewave input again changes direction. Since the input to the tracking A/D converter varies sinusoidally, the master timing output pulses therefrom are produced at the same sinusoidally varying rate, which pulses are used, inter alia, to trigger operation of the transmitting transducer, to actuate the receiver gates and receiver commutator after a suitable delay and to initiate generation of horizontal deflection voltages for the cathode ray tube 78.

It will here be noted that the up-down signal on line 104 to the counter 102 also is supplied as the least significant bit to the D/A converter 100. As will become apparent hereinbelow, this results in interlacing of the horizontal deflection voltages to cathode ray tube 78; that is, horizontal deflection voltages which are produced while the counter 102 is counting up are interlaced with the horizontal deflection voltages which occur when the counter is counting down.

The master timing pulses from the A/D converter 98 (FIG. 1C) are supplied over line 125 as one input to an AND gate (FIG. 1A). The AND gate 126 is provided with two other inputs, one from a flip-flop 133 and another from an inverter amplifier 152 over line 128. For present purposes it will be assumed that the one input thereto from the flip-flop 133 is high to allow the output to go high when the other two inputs are high. The AND gate is supplied over line 128 with transmitter delay pulses of much shorter duration than the master timing pulses supplied thereto over line 125. In the absence of a transmitter delay pulse on line 128, the master timing pulses from the A/D converter 98 pass directly through the AND gate 126. If, on the other hand, a transmitter delay pulse is present on the line 128 at one input to the AND gate when a master timing pulse on line 125 arrives at another input thereto, the leading edge of the output signal from the AND gate is delayed until the end of the transmitter delay pulse. The AND gate 126 thereby serves as a switchable delay circuit which functions, when necessary, to delay the leading edge of the master timing pulses to prevent operation of the transmitting transducer 14 while the receivers 32 are operating. During most of the operating cycle the receivers 32 are gated off when a master timing pulse arrives at the AND gate 126 and no delay of the leading edge thereof is required or provided.

The short delay of the leading edge of selected master timing pulses is necessitated because of the varying rate at which ultrasonic pulses are produced by the transmitting transducer. With the illustrated arrangement wherein, say, 400 ultrasonic pulses are produced at a sinusoidally varying rate during each complete acoustic sweep cycle, the time between pulses may vary from a minimum of, say, 220 microseconds to a maximum of 3000 microseconds. If the distance between the transmitting and receiving transducers is such that approximately 1000 microseconds are required for the pulses to travel therebetween, it will be seen that between 0 to 4 ultrasonic pulses may be in transit between the transducers at any given time. At certain times during a complete cycle of operation a master timing pulse from the tracking A/D converter 98 may be produced during receiver gating operation. The desired signals arriving at the receiving transducer are extremely weak compared to the signals produced by the transmitting transducer, and if the transmitting transducer is allowed to function during the receiving operation, the weak acoustic image field at the receiving transducer is completely masked by the transmitted signal. To prevent transmitter operation at such times the line 128 to the AND gate 126 is pulsed while the receiver gates are open to delay passage of the leading edge of master timing pulses therethrough until after the receiver gates 50 are reclosed.

The master timing pulse output from the AND gate 126 is supplied over line 130 to a transmitter gate generator 132. The generator 132, which may comprise a one-shot triggered by master timing pulses, has an output which is supplied to a power oscillator 134 for on-off control thereof. When the oscillator is turned on by the output from the one-shot 132, a high frequency energy pulse is generated which is supplied to either one of the transmitting transducers 14 or 14', depending upon the setting of a switch 134A, for pulse generation of ultrasonic waves within the medium 11 or medium 12, respectively. Since the master timing pulses occur at a sinusoidally varying rate, it will be apparent that the ultrasonic waves are generated recurrently at the same sinusoidal rate. Transmitter pulses of, say, 6 to 15 microseconds duration typically are employed. In the waveform diagram of FIG. 4 the master timing pulse output from the A/D converter 98 is identified by reference numeral 210, and the AND gate 126 output which controls the transmitter operation is shown as waveform 212. In practice, as described above, some 400 master timing pulses may be produced by the A/D converter 98 for each cycle of sinewave input thereto, but for clarity of illustration only about 1/20th of the total master timing pulses is shown.

Except for those AND gate 126 output pulses which are delayed to avoid simultaneous transmitter and receiver operation, the pulses 212 occur at the same time as the pulses 210, and at the same sinusoidally varying rate. In addition, it will here be noted that although the various pulses 210, 212, 214 and 216 shown in FIG. 4 may be of different width, they are shown of the same size since the time scale employed in FIG. 4 does not allow for differentiating therebetween on that basis.

For similar reasons, the shift of the pulses 210 from the tracking A/D converter during alternate half cycles of the sinewave input 208 provided by application of the up-down signal at line 104 as the least significant bit to the D/A converter is not apparent in the waveforms 210, 212, 214 and 216 of FIG. 4. It will be understood that in the present specification and claims the term "sinusoidally varying rate" used in the description and identification of these pulses is intended to, and does, include the present situation wherein certain pulses are delayed to avoid simultaneous transmitting and receiving operations, and alternate half cycle pulses are advanced (or delayed) for scan interlace.

The transmitter gate output from transmitter gate generator 132 also is supplied as a reset signal to a set-reset type of flip-flop 133. The set terminal of the flip-flop is supplied with master timing pulses from the A/D converter 98 through an inverter amplifier 135, and the flip-flop output is applied as the third input to the AND gate 126. When the flip-flop is set by the cessation of a master timing pulse thereto through the inverter amplifier 135, the output therefrom is high to enable passage of the next master timing pulse through the AND gate 126. The transmitter gate generator 132 is triggered by the output from the AND gate 126, and the output therefrom resets the flip-flop 133 to disable the gate 126. With this arrangement a transmitter delay pulse over line 128 to the gate 126, which occurs during the presence of a master timing pulse from the A/D converter 98 but after the leading edge thereof arrives at the AND gate 126, is prevented from changing the AND gate output since the one input to the AND gate from the flip-flop 133 is low and remains low until the next master timing pulse again sets the flip-flop 133.

The master timing pulses from the AND gate 126 which trigger operation of the transmitter gate generator 132 also are supplied to a pulse delay unit 136 over line 138 for delaying the same a controlled amount. For purposes of illustration the delay unit is shown comprising a shift register 140 which is clocked by a variable frequency oscillator 142. The frequency of the oscillator may be varied between, say, 96 to 320 kHz by means of a range control 144. As will become apparent hereinbelow, the setting of the range control 144 positions the receiver "window," during which time the receiving transducer elements are sampled by opening of the receiver gates 50. In the illustrated arrangement wherein the distance between the transmitting transducer 14 (or 14') and receiving transducer array 16 is variable, adjustment of the delay unit 136 to accommodate the different transit times of pulses traveling therebetween is required. The time required for an input pulse to traverse the shift register and appear at its output depends upon the number of stages in the register and the clocking frequency. For example, with 128 stages the frequency variation from 96 to 329 kHz will allow total delay variations from a maximum of 1333 microseconds to a minimum of 400 microseconds, respectively.

As noted above, the variable frequency oscillator 142 output also clocks the shift register 93 included in the phase lock loop with the voltage controlled delay unit 94 for setting the time $x$ by which the squarewave 206 leads to acoustic field sweep 200 (see FIG. 4). The sinewave 208 derived from the squarewave 206 also leads the acoustic field sweep by the same time $x$, as do the sinusoidally varying master timing pulses 210 from the A/D converter 98. It will here be noted that the shift register 93 in the phase lock loop and the shift register 140 in the delay unit 136 are of the same design and produce the same delay when clocked by the same output from the variable frequency oscillator 142. Consequently, the delayed master timing signal puslses from the shift register 136, identified by reference numeral 214 in FIG. 4, are delayed the same amount of time $x$ by which the tracking A/D input 208 leads the acoustic sweep swee 200, which time $x$, as noted above, equals the transit time of the acoustic field wave from the transmitting transducer 14 to the acoustic field deflecting prisms 28.

The delayed master timing pulses 214 from the delay unit 136 are supplied to various units including a transmitter delay generator 146 over line 148. The generator 146 simply may comprise a one-shot which is triggered on by a delayed master timing pulse and which is turned off by the trailing edge of the receiver power supply gate generator pulse supplied thereto over line 150. The generator 146 output is inverted by inverter amplifier 152 and supplied to the input of the AND gate 126 over line 128 to delay those master timing pulses which occur during the presence of a transmitter delay generator pulse in the manner described above.

The delayed master timing pulses from the delay unit 136 also are supplied to a receiver power supply gate generator 154 for the production of a gating pulse which is supplied to the gated receiver power supply 48 for on-off control thereof. The generator 154, which simply may comprise a one-shot, is provided with adjustable control 155 for control of the pulse width therefrom. In operation, the gated receivers are turned on prior to opening of the receiver gates and turned off after the receiver gates are closed. By shutting off power to the 192 high gain receivers 32 while the receivers are not processing signals from the transducer elements 17, the generation of excess heat therein is avoided without necessitating the use of extensive external cooling means.

Finally, the delayed master timing pulses from the delay unit 136 also are supplied to another delay circuit 158 for additional delay thereof. The delay unit 158, which is included in the receiver gate control circuit, may comprise a one-shot having a gate delay control 160 for control of the delay period. The delayed signal from the unit 158 triggers a receiver gate generator 162 which may comprise a one-shot with width control 164 for control of the width of the receiver gate at the output therefrom. The receiver gate is amplified by amplifier 166 and supplied to various circuits including the receiver gates 50 over lines 51. As noted above, in the absence of a receiver gate signal, the receiver 32 outputs (when the receivers are turned on) are bypassed to ground through the gates 50. Upon receipt of a receiver gate signal, all 192 receiver gates 50 simultaneously are opened for connection of the receiver outputs to the storage units 52. Tht portion of the acoustic image intercepted by the receiver transducer elements during the time the receiver gates 50 are opened is thereby stored. The delay provided by delay unit 158 is equal to the transit time of the acoustic field wave in traveling from the acoustic field deflecting prisms 28 to the receiving array 16. In the illustrated arrangement this time is fixed, whereby the control 160 is set for the required fixed delay. In the waveform diagram of FIG. 4 the delayed receiver gate control pulses from delay unit 158 are identified by reference numeral 216, which pulses are delayed the time $y$ from the pulses 214. It will be apparent that the sum of times $x$ and $y$ substantially equals the transit time of pulses in traveling from the transmitting transducer 14 to the receiving array 16. In the waveform diagram the delay time $y$ is greatly exaggerated for purposes of illustration. A delay time $y$ of approximately 200 microseconds might be experienced in a practical acoustical system.

Timing of the horizontal deflection voltage supplied to the cathode ray tube 78 is under control of the output from the power supply gate generator 154. Horizontal deflection circuitry for the cathode ray tube includes a ramp generator 168 (FIG. 1B) which is triggered in response to the trailing edge of the generator 154 pulses connected thereto over line 167 (from FIG. 1A to FIG. 1B). The ramp voltage generated is applied over line 170 to the horizontal deflection circuitry of the cathode ray tube to horizontally sweep the beam across the face 79 of the tube. It will be seen, then, that horizontal deflection ramp signals are produced in the same number and at the same sinusoidally varying rate at which the delayed receiver power supply gate signals are produced. The variable rate ramp signals for horizontal deflection together with the generally sinusoidal vertical deflection signals combine to produce a raster of substantially uniformly spaced scanning lines. A detailed description of an electromechanical sweep generating system which may be employed in the present system in lieu of the illustrated arrangement may be found in patent application Ser. No. 354,237 filed Apr. 25, 1973, the disclosure of which application specifically is incorporated herein by reference.

The receiver power supply gate generator pulses from generator 154 which gate the receiver power supply on and off (FIG. 1A) also are supplied over line 167 to a commutator delay generator 172 (FIG. 1B) included in the commuation circuit. The trailing edge of the power supply gate pulse functions to trigger the generator 172. The generator 172, which may comprise a one-shot, provides a delay between the end of receiver power supply gating and the start of the commutation process.

The trailing edge of the generator 172 output is supplied as a start signal to a commutator enable flip-flop 171 so set the same for start of the commutation period. The output from the flip-flop 171 is applied to all 192 AND gates 59 to enable the same and to a commutator clock 174 to enable operation thereof. The clock 174 drives a counter 176 having a capacity of 192 for the 192 receiver channels. The output from the counter is supplied to the decoder 66 which, for purposes of description, includes two decoder sections A and B. The A section may comprise, for example, a 12×16 array of gate elements energized by the binary counter output in such a manner as to provide sequential commutator gate pulses at the 192 output lines 177. As mentioned above, the block 59 represents 192 AND gates to which the 192 lines 177 are individually connected. The 192 AND gate outputs are fed through the 192 OR gates 61 to the 192 analog gates 62. When the gates 62 are sequentially opened by signals from the decoder 66, the video information stored in the signal storage units 52 is sequentially passed over four information channels 67 to the four DC analog gates 64 through discharge gates 68 and amplifiers 69. The four gates 64 in the B section of the commutator gates are sequentially switched by commutator gate signals supplied thereto over lines 70 from the B section of the decoder 66.

At the completion of the commutation process, when the commutator has passed the information contained in the 192 signal storage units 52 to the video amplifier 58, a signal is derived from the counter 176 over line 178 which triggers the discharge gate generator 74. The generator 74 simply may comprise a one-shot having a pulse width control 180 for setting the width of the discharge pulse. The discharge gate signal from the generator 74 is applied substantially simultaneously through OR gate 61 to the 192 DC analog gates 62 to open the same and to the four discharge gates 68 to close the same. Under such conditions, the 192 signal storage units 52 are connected through the analog gates 62 and thence bypassed to the common ground 53 through the discharge gates 68. The storage elements (e.g., capacitors) which comprise the storage units are thereby connected to ground for the discharge thereof. As will become apparent from a consideration of the waveform diagram of FIG. 5 described below, the receiver gates 50 are closed during the discharge period to prevent application of receiver signals to the storage units 52 during this time.

The leading edge of the discharge gate signal from the generator 74 also is supplied through an OR gate 182 to the stop terminal of the commutator enable flip-flop 171 to reset the same. The flip-flop output to the commutator clock 174 stops clock operation at the end of the commutation cycle. In addition, the flip-flop output to the gate 59 inhibits passage of commutator switching signals from the decoder 66 to the analog gate circuits 62 while the clock is stopped. The clock remains stopped until started again upon receipt of the next start signal to the commutator enable flip-flop 171 from the delay unit 172. With the clock stopped, the counter 176 is stopped at its rest state of 192. When the clock is restarted, the counter is driven through states 1–192 before the clock again is stopped. With this operation of the clock and counter there is no requirement to reset the counter during normal operation. However, when the equipment is first turned on, or in case of power line transients, counter reset may be required to place the counter in the proper counting state for start of the counting cycle. Counter reset is accomplished by means of a reset generator 184 which is energized by the receiver gate signal supplied thereto over line 186. The reset generator output is applied both to the counter to reset the same and to the stop terminal of the commutator enable flip-flop 171 through the OR gate 182 to reset the same if it has not already been reset by application of a discharge gate pulse thereto. It will be seen, then, that the reset generator serves to stop the clock and reset the counter to the reset state of 192 if the clock and counter are not already in such condition and state before commencement of a commutation cycle.

Although the operation of the ultrasonic camera system and method of this invention is believed to be apparent from the above description, a brief description thereof with reference to the waveforms of FIGS. 4 and 5 now will be made. As the motor 29 drives the prisms 28, the acoustic image field produced by ultrasonic waves traveling through the specimen 8 (such as a patient) is focused by lenses 23 and 24 and vertically deflected by the counterrotating prisms 28, whereby the field scans the line of receiver transducer elements 17 (FIG. 4, waveform 200). During such scanning operation, a symmetrical squarewave master timing signal (FIG. 4, waveform 202) is produced at the photocell 83 output, which output is delayed, filtered and then converted by the tracking A/D converter 98 to master timing pulses (FIGS. 4 and 5, waveform 210) which occur at the sinusoidally varying rate of waveform 208 from filter 96. The master timing pulses from the AND gate 126 (FIGS. 4 and 5, waveforms 212) initiate transmitter gate pulses 218 (FIG. 5) which enable the oscillator 134 for energization of the transmitter transducer 14 (or 14') for periods of, say, 6 to 15 microseconds.

It will here be noted that if a master timing pulse, such as pulse 210A shown in FIG. 5, from the A/D converter 98 is initiated during the presence of a transmitter delay pulse, such as pulse 220 of FIG. 5, the leading edge of the master timing pulse designated 212A from the AND gate 126 is delayed until termination of the transmitter delay pulse 220. The transmitter pulse designated 218A is similarly delayed, as are all of the corresponding subsequent receiver functions for receiving and processing the delayed ultrasonic pulse. The transmitter delay pulses 220 are generated by the transmitter delay generator 146 which is triggered by delayed master timing pulses 214 from the delay unit 136. As seen in the waveform diagram of FIG. 5, the amplified and inverted transmitter delay pulse 220 functions to prevent transmitter operation from time T2 to T7, during which the receivers 32 are energized.

The ultrasonic wavefield generated by the transmitting transducer 14 during the period of pulse 218 (FIG. 5), which is initiated at time T1, travels through the object 8 and composite lens system to be focused on the face of the receiving transducer array 16, whereupon electrical signals in response to the amplitude of the impinging acoustic wave image are produced by the line of transducer elements 17. The delayed master timing pulse 214 from the delay unit 136 not only triggers the transmitter delay generator 146, as described above, for generation of transmitter delay pulse 220 but also initiates operation of the gated receiver power supply which provides power to the receivers 32, as indicated by waveform 222, for energization thereof.

The delayed master timing pulse 214 is further delayed by the receiver gate delay circuit 158 and subsequently triggers the receiver gate generator 162 to produce a receiver gate control signal 224 at time T4. The delay from time T2, when the receivers 32 are turned on, to time T4, when the receiver gates 50 are opened, is sufficient to permit stabilization of the receiver operation. (In the present arrangement, this also constitutes the transit time of the ultrasonic wavefield in traveling between the counterrotating prisms 28 and receiving transducer array 16.) When the receiver gates 50 are opened, the storage units 52 are charged to thereby capture, in effect, the acoustic image field amplitude existing at the line of transducer elements 17 at that time, which line of information subsequently is transferred to the cathode ray tube during the commutation period. The control 155 at the receiver power supply gate generator is set for termination of the receiver power supply 222 at time T7, a short time after the end of the receiver gate signal 224 at time T6.

Before the commutation begins, begins, the commutator clock 174 is stopped and the counter 176 is reset (if necessary) by the signal 226 from the reset generator 184, which is triggered by the leading edge of the receiver gate pulse 224 at time T4. The trailing edge of the receiver power supply gate pulse 222 triggers the ramp generator 168 to initiate a ramp signal 228 at time T7 for horizontal deflection of the cathode ray tube beam. The relatively low frequency sinewave 204 of, say, 7.5 cycles per second, shown in FIG. 4, for vertical deflection changes only a minimal amount during this horizontal sweep.

The trailing edge of the receiver power supply gate generator pulse 222 also triggers the commutator delay generator 172 for generation of the commutator delay pulse 230. The trailing edge of the pulse 230 is supplied as a start signal to the commutator enable flip-flop 171, thererby initiating commutation at time T8. During the commutation period the clock 174 drives the counter 176, the output of which is decoded by decoder 66. The decoder output, in turn, drives the commutator 60, whereupon the information stored in the signal storage units 52 is read out to the video amplifier 58. The commutation signal designated 232 in FIG. 5 simply is intended to illustrate the time period from time T8 to T9 over which commutation takes place and does not illustrate the individual commutator clock, counter or gate signals generated during this period.

At the end of the commutation period, when the counter 176 reaches a count of 192, the discharge gate generator 74 is triggered to produce a discharge pulse 234. The leading edge of this pulse is applied to the stop terminal of the commutator enable flip-flop 171 through the OR gate 182 to reset the same, thereby stopping the clock while the counter 176 is at the rest state at count of 192 and disabling the AND gates 59. The discharge pulse 234 also is applied to all 192 gate circuits 62 (through OR gates 61) and to all four gate circuits 68 for discharge of the storage units 52 therethrough. The ramp pulse 214 terminates at some time, say T10, after the commutation period, the gate discharge pulse 234 terminates at time T11, and the system is in condition for producing the next horizontal line of information at the face of the cathode ray tube.

The invention having been described in detail in accordance with the requirements of the Patent Statutes, various changes and modifications may suggest themselves to those skilled in this art. For example, the patient or specimen may be placed within a liquid medium to which the transmitting and receiving transducers are coupled, rather than coupling through accoustically transparent membranes as shown. Also, although a transmission type of system and method of acoustical imaging have been described, it will be apparent that the invention may be employed in a reflective type of system, wherein the receiving transducer responds to forward or backscattered acoustical waves produced by generator 14', rather than transmitted waves from generator 14. With such an arrangement the range control would be set to provide a receiver window dependent upon the overall distance which the reflected acoustic wave travels from the transmitting to the receiving transducers. In addition, as suggested above, it would be a simple matter to generate master timing pulses at a constant rate, rather than at a sinusoidal rate as shown. A pulse generator which operates at a constant pulse repetition rate, for example, could be used to provide master timing pulses, rather than the illustrated tracking A/D converter 98 and associated circuitry. With master timing pulses a constant repetition rate, more scan horizontal lines would be generated adjacent the top and bottom of the screen where the vertical scan is changing at the slowest rate.

It will be apparent that the display at the face 70 of the cathode ray tube 78 may be converted by a scan converter 249, as seen in FIG. 1B, to signals which may be employed by a conventional television type of monitor or display. In another modification, the gated receiver outputs could be supplied to a visual display such as a 192×400 light source array with suitable commutator switching to step the 192 inputs to the array to sequentially energize alternate lines thereof. In such an arrangement all 102 inputs would be applied simultaneously to the display rather than sequentially. Also, although simultaneous actuation of all of the receiver gates 50 is shown, it will be apparent that sequential operation thereof to accommodate for slightly different arrival times of the acoustic field at the transducer elements 17 of the array may be provided if, in fact, the waves arrive at slightly different times. In any event, the receiver gates are operated substantially simultaneously, if not precisely simultaneously. In addition, various features of this invention are applicable to continuous wave systems in which the specimen is continuously insonified rather than being recurrently insonified as shown, as well as to continuous and pulse doppler systems. For example, the substantially simultaneus storage of amplified signals representative of at least a portion of an acoustic image field and the sequential sampling of such stored signals may be employed with other such ultrasonic image camera systems. It is intended that these and other such modifications which fall within the spirit and scope of the invention will be covered by the appended claims.

We claim:

1. In a system for providing a real time signal representative of an acoustic image field traveling in a fluid medium;

ultrasonic wave generating transducer means for providing ultrasonic waves to insonify an object under observation coupling to the fluid medium;

ultrasonic receiving transducer means including a plurality of transducer elements for converting at least a portion of an acoustic image field received from the object to electrical signals;

means for focusing said acoustic image field from said object at the receiving transducer elements;

means for relatively sweeping said acoustic image field and receiving transducer elements to expose the transducer elements to a full focused acoustic image field;

a plurality of electrical signal storage means each capable of storing only an instantaneous signal value;

controlled first connecting means operable between signal conducting and nonconducting conditions for connecting individual receiver transducer elements to individual storage means;

means for recurrently controlling said first connecting means for recurrent simultaneous operation in the signal conducting condition for a short time interval for simultaneously storing in said individual storage means in instantaneous signal value related to the amplitude of electrical signals produced by said associated receiving transducer elements;

controlled second connecting means operable between signal conducting and nonconducting condition for connecting to the individual storage means; and means operable following signal conducting operation of the first connecting means for sequential signal conducting operation of saiad second connecting means to provide a composite signal representative of the portion of the acoustic image field impinging upon the receiving transducer at the time the signals from the receiving transducer elements are simultaneously stored.

2. In a system for providing a signal representative of an acoustic image field travelling in a fluid medium;

ultrasonic wave generating transducer means for producing ultransonic waves to insonify an object under observation coupled to the fluid medium;

ultrasonic receiving transducer means including a plurality of transducer elements for converting at least a portion of an acoustic image field received from the object to electrical signals;

a plurality of electrical signal storage means each capable of storing an instantaneous signal value;

first connecting means for connecting individual receiver transducer elements to individual storage mens for simultaneously storing in said individual storage means an instantaneous signal value related to the amplitude of electrical signals produced by said associated receiving transducer elements; and second connecting means operable following operation ot said first connecting means for sequentially connecting to the individual storage means to provide a composite signal representative of the portion of the acoustic image field impinging upon the receiving transducer at the time the signals from the receiving transducer elements are simultaneously stored.

said second connecting means comprising a first group of analog gates equal in number to said electrical signal storage means and a second group of a fewer number of analog gates connected to the outputs from said first group of analog gates to reduce adverse capacitance effects in connecting to the signal storage to provide said composite signal.

3. In a system for providing a signal representative of an acoustic image field traveling in a fluid medium;

ultrasonic wave generating transducer means for producing ultrasonic waves to insonify an object under observation coupled to the fluid medium;

ultrasonic receiving transducer means including a plurality of transducer elements arranged in a linear array for converting at least a portion of an acoustic image field received from the object to electrical signals;

a plurality of electrical signal storage means each capable of storing an instantaneous signal value;

first connecting means for connecting individual receiver transducer elements to individual storage means for simultaneously storing in said individual storage means an instantaneous signal value related to the amplitude of electrical signals produced by said associated receiving transducer elements;

second connecting means operable following operation of said first connecting means for sequentially connecting to the individual storage means to provide a composite signal representative of the portion of the acoustic image field impinging upon the receiving transducer at the time the signals from the receiving transducer elements are simultaneously stored;

means for relatively sweeping at a varying rate the transducer elements and acoustic image field in a direction substantially orthogonal to the longitudinal dimension of the transducer array;

means for generating timing pulses at a varying rate dependent upon the varying rate of sweep motion of the transducer elements with respect to the acoustic image field; and means including said timing pulses for controlling said ultrasonic wave generating transducer means for producing pulses of ultrasonic waves at a rate dependent upon the rate of said timing pulses.

4. In a system as defined in claim 3 including:

a cathode ray tube which includes a screen upon which a stream of electrons impinges to produce a spot;

first deflection means for effecting scanning motion of the spot in one direction across the screen in synchronization with said means for relatively sweeping the transducer elements and acoustic image field;

second deflection means for effecting scanning motion of the spot in an orthogonal direction in synchronization with said timing pulses; and means for applying said composite electrical signal from said second connecting means to said cathode ray tube for control of the current density of the electron stream.

5. In a system as defined in claim 4 including means for focusing the acoustic image field present at an object plane within said object at an image plane at the receiving transducer means such that a visual display is provided at the screen of the cathode ray tube of a section of the object at the object plane of the focusing means.

6. In a system or providing a signal representative of an acoustic image field traveling in a fluid medium;

ultrasonic wave generating transducer means for producing ultrasonic waves to insonify an object under observation coupled to the fluid medium;

ultrasonic receiving transducer means including a plurality of transducer elements for converting at least a portion of an acoustic image field received from the object to electrical signals;

means for relatively sweeping at a varying rate the receiving transducer elements and acoustic image field;

a plurality of electrical signal storage means each capable of storing an instantaneous signal value;

first connecting means for connecting individual receiver transducer elements to individual storage means for simultaneously storing in said individual storage means an instantaneous signal value related to the amplitude of electrical signals produced by said associated receiving transducer elements; and second connecting means operable following operation of said first connecting means for sequentially connecting to the individual storage means to provide a composite signal representative of the portion of the acoustic image field impinging upon the receiving transducer at the time the signals from the receiving transducer elements are simultaneously stored, said first and second connecting means being sequentially operated at a varying rate dependent upon the varying rate of relative sweep of the receiving transducer elements and acoustic image field.

7. In a system as defined in claim 6 wherein said first and second sequentially operated connecting means are cyclically operated at a generally sinusoidally varying rate.

8. In a system as defined in claim 7 wherein said ultrasonic wave generating transducer means are cyclically operated at a generally sinusoidally varying rate, and means for preventing operation of said wave generating transducer means during operation of said first connecting means.

9. In a system as defined in claim 8 wherein said preventing means includes means for delaying operation of said wave generating transducer means during operation of said first connecting means.

10. In a system as defined in claim 7 including means for discharging all of said signal storage means following sequential operation of said first and second connecting means in preparation for another operation of said first and second connecting means.

11. In a system as defined in claim 10 wherein said second connecting means includes a plurality of analog gate circuits which are sequentially operated when providing said composite signal and which also are operable substantially simultaneously, said signal storage means being discharged through said substantially simultaneously operated analog gate circuits.

12. In a system as defined in claim 10 wherein said second connecting means comprise a plurality of analog gate circuits which are sequentially operated following operation of said first connecting means;

means for operating said analog gate circuits substantially simultaneously following said sequential operation thereof; and means for bypassing the output from said substantially simultaneously operated analog gate circuits to ground for discharge of said signal storage through said substantially simultaneously operated analog gate circuits.

13. In a system as defined in claim 1 wherein:

said first connecting means includes;

a plurality of gate circuits operated between open and closed conditions;

a plurality of amplifiers in series with said gate circuits, and means for energizing said amplifiers while said gate circuits are open and for intervals preceding and following the gate circuit open condition.

14. In a system for providing an electrical signal representative of an acoustic image field traveling in a fluid medium;

ultrasonic wave generating transducer means for producing recurrent pulses of ultrasonic waves at a continuously varying pulse rate to insonify an object under observation coupled to the fluid medium;

an ultrasonic receiving transducer including a plurality of transducer elements operated at the same continuously varying rate as said wave generating transducer means for converting at least a portion of an acoustic image field received from the object to electrical signals; and means for relatively sweeping said receiving transducer means and acoustic image field at a continuously varying rate to expose the receiving transducer elements to a full acoustic image field at a synchronous rate with the operation of the recurrent pulse producing ultrasonic wave generating transducer means.

15. In a system as defined in claim 14 wherein said means for relatively sweeping said receiving transducer and acoustic image field includes a pair of counterrotating acoustic wedges in the path of the acoustic image field operating at a constant rate of rotation to produce a sinusoidal sweep of the acoustic image field at the receiving transducer.

16. In a system as defined in claim 14 including:
a cathode ray tube having a screen upon which a stream of electrons impinges to produce a spot deflectable in orthogonal directions across the screen;
means for generating timing pulses at a continuously varying rate dependent upon the rate of relative sweep motion of said receiving transducer and acoustic image field;
means under control of said timing pulses for timing the production of recurrent pulses of ultrasonic waves by said ultrasonic wave generating transducer means;
first deflection means for effecting scanning movement of said spot in one direction across the screen in synchronism with said means for relatively sweeping said receiving transducer means and acoustic image field; and
second deflection means including a ramp generator for effecting scanning movement of said spot in an orthogonal direction across the screen in synchronism with said timing pulses,
said first and second deflection means operating to produce substantially evenly spaced lines across said screen.

17. In a system as defined in claim 16 wherein said timing pulses are generated at a sinusoidally varying rate and wherein said means for generating timing pulses includes means for advancing said timing pulses during alternate half cycles of said sinusoidally operated first deflection means for interlacing of said spot.

18. Apparatus for real time visual imaging of physical characteristics of the interior of a body comprising:
means including transmitter transducer means for recurrently insonifying said body with recurrent ultrasonic pulses at a continuously varying pulse rate to produce an acoustic image field;
receiver transducer means;
means for acoustically coupling said receiver transducer means to said body to develop receiver transducer signals in response to the acoustic image field thereat;
means including said acoustic coupling means for recurrently sweeping the acoustic image field past said receiver transducer means at a continuously varying rate while said transmitter and receiver transducers and said body remain relatively stationary;
visual indicating means including a screen and means for producing an indicating spot on said screen;
first deflection means for effecting scanning movement of said spot in one direction across the screen in synchronism with said acoustic image field sweeping means;
second deflecting means for effecting scanning movement of said spot in an orthogonal direction across the screen in synchronism with said transmitted pulses; and
means for applying said receiver transducer means signals to said indicating means to control the intensity of said indicating spot,
there being substantially evenly spaced lines produced across said screen.

19. The apparatus for real time visual imaging of physical characteristics of the interior of a body as defined in claim 8, wherein said recurrent ultrasonic pulses are produced at a sinusoidally varying rate by said insonifying means.

20. The apparatus for real time visual imaging of physical characteristics of the interior of a body as defined in claim 19, wherein:
said acoustic image field is swept past said receiver transducer means at a sinusoidally varying rate by said acoustic coupling means; and including
means for synchronizing operation of said insonifying means with said acoustic image field sweeping means and deflection of said spot in one direction across the screen.

21. In a method of producing a signal representative of an acoustic image field traveling in a fluid medium comprising:
generating recurrent ultrasonic wave pulses at a continuously varying rate to insonify an object under observation;
receiving at receiving transducer means at least a portion of an acoustic image field from the object;
relatively sweeping said receiving transducer means and acoustic image field at a continuously varying rate to expose the receiving transducer to a full acoustic image field; and
synchronizing the rate of pulse generation of the recurrent ultrasonic waves with the sweep rate of pulse generation of the recurrent ultrasonic waves with the sweep rate of said receiving transducer means and acoustic image field.

22. In a method as defined in claim 21 including generating said ultrasonic wave pulses at a generally sinusoidally varying rate and sweeping said receiving transducer and acoustic image field at a synchronous rate therewith.

23. In a method as defined in claim 21 wherein said receiving transducer means comprises an array of transducer elements, said method including;
connecting the transducer elements to individual storage elements to store substantially simultaneous instantaneous values of signals obtained therefrom at a synchronous rate with the generation of ultrasonic pulses; and subsequently
sequentially sampling the stored instantaneous value of signals to obtain a composite video signal therefrom.

24. In a method as defined in claim 23 including synchronizing said generation of ultrasonic wave pulses and sweeping of said receiving transducer means and acoustic image field at a generally sinusoidally varying rate.

25. In a method as defined in claim 23 including discharging said storage elements after sequentially sampling the stored signals.

26. In a method of producing an electrical signal representative of an acoustic image field traveling in a fluid medium comprising:
generating ultrasonic waves to insonify an object under observation;
receiving at a plurality of acoustic transducer elements at least a portion of an acoustic image field from the object and focused at the transducer elements;
relatively sweeping said acoustic image field and acoustic transducer elements to expose the transducer elements to a full focused acoustic image field;
substantially simultaneously recurrently gating for short time intervals signals produced by the transducer elements to associated individual storage elements for recurrently simultaneously storing in the storage elements the instantaneous value of signals related to the signals produced by the associated transducer elements;

sequentially sampling the stored instantaneous value of signals to obtain a composite signal representative of at least a portion of the acoustic image field in a plane normal to the line of propagation of the acoustic image field from the object to the acoustic transducer elements, and repeating the generating, receiving, gating, and sampling steps without affecting focusing of the acoustic image field at the transducer elements.

27. In a method as defined in claim 26 including:
substantially simultaneously amplifying the signals from the transducer elements before storing the same.

28. In a method as defined in claim 26 wherein said sweeping, generating, receiving, gating and sampling steps are repeated at a varying rate.

29. In a method of producing an electrical signal representative of an acoustic image field traveling in a fluid medium, comprising;

generating ultrasonic waves to insonify an object under observation;

receiving at a plurality of acoustic transducer elements at least a portion of an acoustic image field from the object;

substantially simultaneously gating signals produced by the transducer elements to associated individual storage elements for simultaneously storing the instantaneous value of signals related to the signals produced by the transducer elements;

sequentially sampling the stored instantaneous value of signals to obtain a composite signal representative of at least a portion of the acoustic image field in a plane normal to the line of propagation of the acoustic image field from the object to the acoustic transducer elements, and recurrently repeating the generating, receiving, gating and sampling steps at a generally sinusoidally varying rate.

30. A method of real time visual imaging of physical characteristics of the interior of a body comprising:

insonifying said body with recurrent ultrasonic pulses at a varying pulse rate from a source thereof to produce recurrent acoustic image fields therewithin;

developing at a receiver transducer means acoustically coupled to said body signals responsive to the acoustic image fields;

recurrently relatively sweeping the acoustic image field and receiver transducer means at a varying rate;

deflecting a spot on the face of a visual display in one direction thereacross in synchronism with the recurrent sweeping of the acoustic image field, and in an orthogonal direction thereacross in synchronism with operation of said source of ultrasonic pulses to produce evenly spaced lines on the face of the visual display; and controlling the intensity of said spot in accordance with the intensity of the acoustic image field at the receiver transducer.

31. The method of real time visual imaging of physical characteristics of the interior of a body as defined in claim 30 including producing said ultrasonic pulses at a sinusoidally varying pulse rate.

32. The method for real time visual imaging of physical characteristics of the interior of a body as defined in claim 30 wherein;

said acoustic image field is swept across said receiver transducer means at a varying rate; and including synchronizing ultrasonic pulse production with acoustic image sweeping and deflection of said spot in one direction across the face of the visual display.

33. The method of real time visual imaging of physical characteristics of the interior of body as defined in claim 31 including focusing said acoustic image field from said body at said receiver transducer means.

* * * * *